(12) United States Patent
Beierling

(10) Patent No.: US 6,219,402 B1
(45) Date of Patent: Apr. 17, 2001

(54) METHOD AND DEVICE FOR TESTING AN OBJECT

(76) Inventor: Hans-Jürgen Beierling, Holtgrevenstrasse 22, D-33100, Paderborn (DE)

( * ) Notice: Subject to any disclaimer, the term of this patent is extended or adjusted under 35 U.S.C. 154(b) by 0 days.

(21) Appl. No.: 09/398,145

(22) Filed: Sep. 17, 1999

(30) Foreign Application Priority Data

Sep. 22, 1998 (DE) .............................................. 198 43 397

(51) Int. Cl.$^7$ .............................................. G01N 23/083
(52) U.S. Cl. .............................................. 378/61; 378/4
(58) Field of Search .............................. 378/4, 58, 61, 378/208

(56) References Cited

U.S. PATENT DOCUMENTS 3,873,837 * 3/1975 Palermo .................................. 378/61
3,903,416 * 9/1975 Fox ........................................ 378/61
4,785,354 * 11/1988 Nakamura et al. ...................... 378/4

FOREIGN PATENT DOCUMENTS 195 42 762  5/1997 (DE) .
0 471 096   2/1992 (EP) .
0 652 433   5/1995 (EP) .

* cited by examiner

*Primary Examiner*—David V. Bruce
*Assistant Examiner*—Drew A. Dunn
(74) *Attorney, Agent, or Firm*—Browdy & Neimark

(57) ABSTRACT

In the method of testing a folded-seam connection (2) of a receptacle (1), a sectional image through the folded-seam connection (2) is generated in at least a partial segment (3) of the folded-seam connection (2) by way of an X-ray computer tomographer. The device for executing this method has at least one computer-tomography device (CT device) that has at least one X-ray source (10) and one X-ray detector (11). A holding device (30) holds the receptacle (1) with the folded-seam connection (2) such that at least a partial segment (3) of the folded-seam connection (2) is located in the beam path (S) between the X-ray source (10) and the X-ray detector (11). The holding device (30) and/or the receptacle (1) can rotate relative to the X-ray source (10) with the X-ray detector (11) such that the partial segment (3) of the folded-seam connection (2) is rotated, in at least one angular region (δ), about a first axis of rotation (20) extending through the beam path (S), with the partial segment (3) of the folded-seam connection (2) remaining in the beam path (S).

8 Claims, 4 Drawing Sheets

METHOD AND DEVICE FOR TESTING AN OBJECT

BACKGROUND OF THE INVENTION

1. Technical Field of the Invention

The invention relates to a method for testing an object, in which a sectional image of the object is generated in at least a partial segment of the object by means of an X-ray computer tomographer. In the method, the object is clamped in a holding device, with which at least the partial segment is brought, in direction extending transversely to the segment, into a beam path between an X-rag source and an X-ray detector of the computer tomographer; then, the object and the holding device are pivoted, in at least one angular region, and relative to the X-ray source with the X-ray detector, about a first axis that extends through the partial segment and the beam path, with the partial segment remaining in the beam path. In specific angular increments, the X-ray detector generates a radiogram, and a cross-sectional image through the partial segment is reconstructed from these radiograms. The invention further relates to a device for executing the method.

2. Prior Art

A device of this type is known from EP 0 471 096 A1. The subject is a rim-mounted tire that is received at its end face in a holding device, which can travel on an adjusting sliding element on a pivoting device such that the pivoting axis of the pivoting device approximately axially passes through a tire cross section.

The beam fan of the X-ray device passes through the tire perpendicular to the pivoting axis; a holding arm of the beam receiver is positioned close to the tire and, depending on the pivoting position, is located in the open space of the rim or extends through it. The X-ray device is held on a sliding element that can be displaced perpendicular to the beam path and perpendicular to the pivoting axis of the tire, so a plurality of individual images of the one tire cross section can be generated corresponding to the different pivoting positions and the different displacement positions, and used in a cross-sectional representation. Further cross sections of the tire can only be obtained after the tire has been unclamped and fixed in a different angular position.

A computer tomographer that is particularly provided for testing cross sections of rim-mounted tires is known from EP 0 652 433 A. The tire is held in a holder about a pivoting axis perpendicular to the beam fan of an X-ray device. The tire can be displaced, in a sliding element, perpendicular to the pivoting axis and parallel to the tire plane, so the pivoting axis can be shifted into the one or the other of the two tire cross sections through which the beam fan passes, corresponding to the displacement positions. It is not possible to execute and allaround testing of the tire.

Numerous receptacles, such as sheet-metal boxes or the like, have some sort of folded-seam connections. For example, the lids or bottoms of tin cans are often connected to the jacket part through a folded-seam connection. Different forms of folded-seam connections are selected depending on the material and stress of the package. For sealing purposes, a sealing element may also be incorporated into a folded-seam connection.

The quality of a folded-seam connection depends on, among other things, the correct position of the material layers in the fold. At the present time, the quality can only be tested in a seal test (pressure test), mechanical stress tests or an external geometrical check of the dimensions. Cutting open the fold and removing and examining segments from the fold at defined or critical locations is the only way to obtain information about the correct material connection inside the fold. This is a destructive test, so, of course, only sample testing can be performed on packages in this method. Furthermore, the mechanical cutting open of the folded-seam connection can mechanically influence the sectional surface to be examined such that the original state of the folded-seam connection is no longer apparent. The test result is therefore skewed.

Because numerous boundary layers are present in a folded-seam connection, it is not possible to employ ultrasound methods or the like in testing.

OBJECT AND SUMMARY OF THE INVENTION

It is the object of the present invention to make the method described at the outset applicable for testing a folded-seam connection of a receptacle, and to provide a device for executing this method, with which it is possible to obtain information about the completely-correct material connection within a circumferential fold without destroying the object. This method and this device are further intended to operate quickly and inexpensively.

This object is accomplished in that the object is a receptacle having a folded-seam connection between a lid and/or a bottom and a jacket; to generate a sectional image through this folded-seam connection in the radial direction, the holding device is pivoted about the first axis; to generate at least one further sectional image through at lest one further partial segment of the folded-seam connection, the receptacle is rotated along its circumference in the holding device until the further partial segment of the folded-seam connection is located in the beam path (S), and the holding device and the receptacle are then pivoted about the first axis again to generate an image.

With the use of an X-ray computer tomographer to examine the folded-seam connection, a precise profile contour of a multi-layer folded-seam connection can be obtained, so material of varying density, such as metal, a hollow space, a plastic seal, another metal layer, etc., can be superposed. In this way, the same sectional images are obtained as in the cutting open of the fold, without the receptacle being destroyed or the sectional surface being influenced.

For the test, at least a partial segment of a folded-seam connection of the receptacle is brought, in a direction transverse to the longitudinal direction of the fold, into a beam path between an X-ray source and an X-ray detector of a computer tomographer. Then, the receptacle and/or the X-ray source with the X-ray detector are rotated relative to one another such that the partial segment of the folded-seam connection is rotated in at least one angular region about a first axis extending through the beam path. The partial segment of the folded-seam connection remains in the beam path. In specific angular increments, the X-ray detector generates a radiogram, and a cross-sectional image through the partial segment of the folded-seam connection is reconstructed from these X-ray images.

For executing the method, the device has at least one computer-tomography device (CT device) that has at least one X-ray source and one X-ray detector. The device further includes at least one holding device for a receptacle having a folded-seam connection; the holding device holds the receptacle such that the folded-seam connection is located, at least on the partial segment, in the beam path between the X-ray source and the X-ray detector, and the holding device and/or the receptacle can be rotated relative to the X-ray source with the X-ray detector such that the partial segment of the folded-seam connection is rotated, in at least one angular region, about a first axis of rotation that extends through the beam path; the partial segment of the folded-seam connection remains in the beam path.

Usually, a line detector that extends in the desired sectional-image plane is used as the X-ray detector. The detector can, however, also be displaced along a path within the sectional-image plane, and travel along the path, in order to generate a radiogram. In this case, "beam path" refers to the entire beam path between the X-ray source and the detectable detector range. The central axis between the X-ray source and the central point of the path along which the detector can travel would then be the optical axis of this system.

The first axis about which the partial segment of the folded-seam connection is rotated preferably extends directly through the partial segment of the folded-seam connection and, preferably, also exactly perpendicular through the optical axis of the beam path.

The receptacle and/or the X-ray source in the X-ray detector are preferably rotated relative to one another by at least an angle in the range between 180° and 360° to generate a sectional image. The broader the angular region of rotation, the better the image quality. This is especially the case when only regions of the object, such as only the fold in the present case, must be reconstructed without requiring the object, that is, the entire receptacle, to be located completely within the beam path, i.e., the fan beam of the X-ray source. Reconstruction algorithms that are adapted to the respective task i.e., the respective object, are then used to reconstruct such an image through a partial region of the entire object.

Ideally, of course, the object can be rotated by 360°. It has been found, however, that a suitable algorithm attains highly-satisfactory images without the creation of artifacts, even with a rotation of only 210°.

It is especially advantageous when X-ray images that have only been generated in specific angular regions are used to reconstruct a sectional image. Thus, it is practical not to use the generated images in which, for example, a further corner of the receptacle, in other words, a further folded-seam connection, is located in the beam path, for reconstruction in the angular regions.

If the angular regions in which the images cannot be assessed are known prior to the test, it is practical and faster not to generate any X-ray images in these particular angular regions. Naturally, however, it is also possible that the angular regions that are not used for reconstructing a sectional image are determined with the aid of X-ray images generated in these angular regions when the sectional image is reconstructed. This can be effected, for example, in that radiograms are recorded continuously over the entire angular region over which the receptacle is rotated, and the unusable radiograms are filtered out in the reconstruction. Alternatively, the radiograms can be continuously tested during the rotating process. If this test reveals that the receptacle is located in a region in which no radiograms can be used, the width of the angular increment is increased, for example, until an angular region is reached in which the radiograms can again be used for reconstruction.

The method is especially well-suited for, among other application, testing receptacles that are rotationally symmetrical and have a jacket and two end walls, with the folded-seam connections respectively connecting the end walls to the jacket. The receptacles can be, for example, barrels, containers or drums in which the folded-seam connection connects the lid or the bottom to the jacket. In principle, however, a longitudinal fold on the jacket can be tested in these types of receptacles.

This type of receptacle is preferably clamped in a holding device such that a first partial segment of a folded-seam connection in the beam path between the X-ray source and the X-ray detector. To generate a sectional image in the radial direction through the partial segment of the folded-seam connection, the holding device and the receptacle are rotated about a first axis, which extends perpendicular to the sectional-image plane and through the partial segment of the folded-seam connection. To generate one or more further sectional images through one or more further partial segments of the folded-seam connection, the receptacle is subsequently rotated along its circumference, i.E.k, about its axis of symmetry, in the holding device until the desired partial segment of the folded-seam connection, at which the respective further sectional image is to be generated, is located in the beam path. The holding device and the receptacle are then rotated about the first axis again, and another radiogram is generated. The folded-seam connection between the lid and the jacket or the bottom and the jacket, respectively, can thus be tested quickly and simply over the entire circumference.

To generate sectional images through one or more partial segments of the folded-seam connection between the oppositely-located lid and the jacket, and the bottom and the jacket, respectively, the holding device and the receptacle are preferably rotatable by 180° about a second axis, which extends through the central point of the receptacle and perpendicular to its axis of symmetry.

The holding device is embodied such that it has corresponding clamping elements or the like, with which the receptacle can be fixed in the respective position in the beam path.

The holding device is disposed, with the X-ray source and the X-ray detector, in a shielding space that only permits the maximum allowable doses of X-rays to be emitted. This space has an opening that can be closed for transferring a receptacle into the holding device and removing it from the device.

BRIEF DESCRIPTION OF THE DRAWINGS

The invention is described in detail by way of an embodiment, with reference to the attached drawing, which shows in.

DETAILED DESCRIPTION OF THE PREFERRED

EMBODIMENTS OF THE INVENTION

The figures show a testing device for testing the folded-seam connection (2) between a lid or the bottom (5, 6) and a jacket (40 of a barrel (1).

Figure 1:
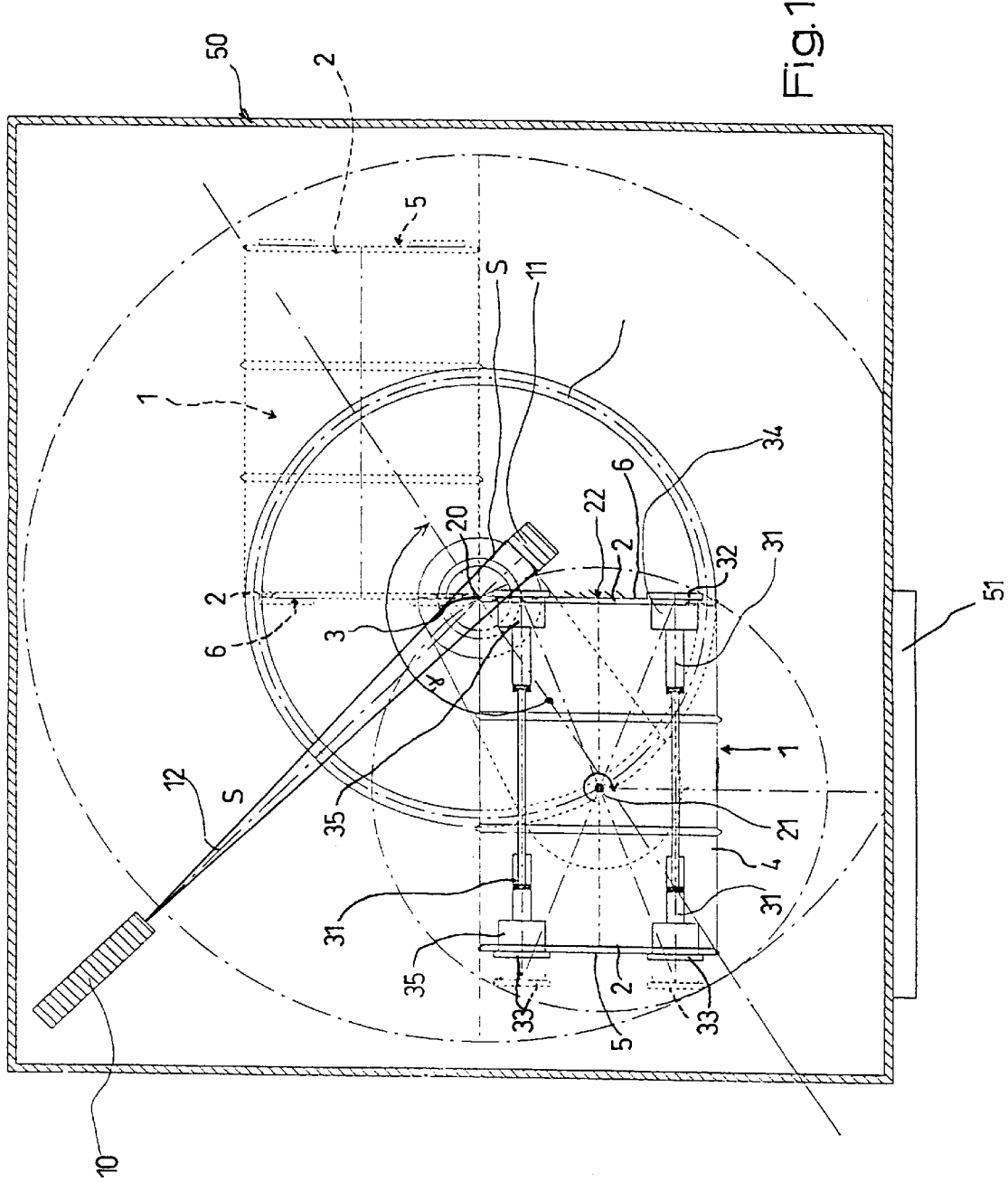
FIG. 1 a schematic plan view of a device according to the invention for testing a barrel located in an initial position (the end position of the barrel is shown as a dashed line)
Figure 2:
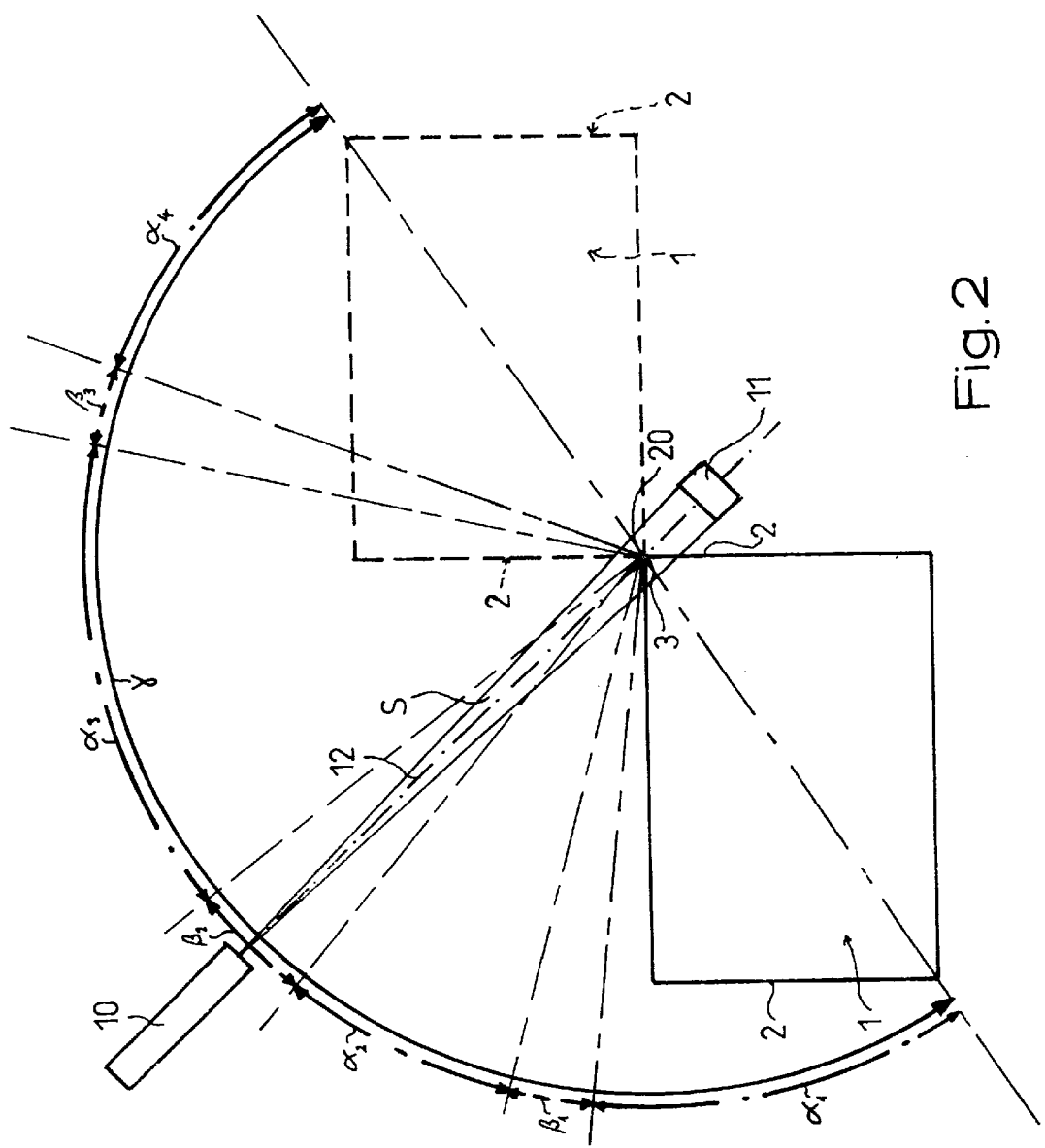
FIG. 2 a further schematic plan view of the device according to FIG. 1, but in a simplified representation for explaining the different angular regions.
Figure 3:
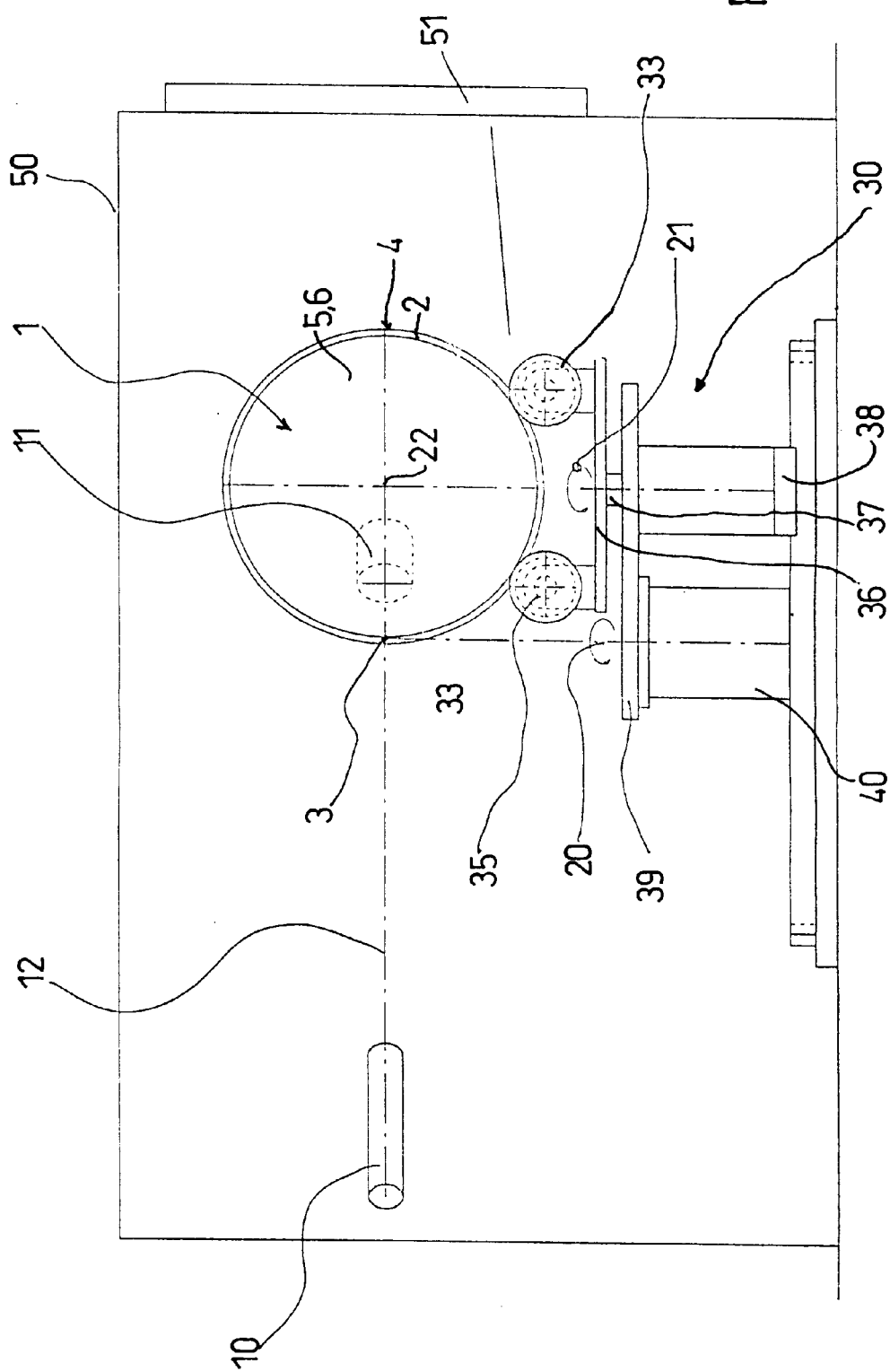
FIG. 3 a schematic side view of the device according to FIG. 1, in the longitudinal direction of the barrel in the initial position.

As can be seen from FIGS. 1 through 3, the device includes an X-ray source (10) and an X-ray detector (11), which are connected to a computer (not shown) that generates a computer-tomographic image from the radiograms. In the present illustrated embodiment, the detector (11) is a line detector that detects the beam fan originating from the X-ray source (10) in a horizontal plane. The beam fan emitted by the X-ray source (10), which is detected by the detector (11), is referred to as the beam path (S) between the X-ray source (10) and the X-ray detector (11).

The testing device further includes a holding device (30) that holds the barrel (1) such that a partial segment (3) of a folded-seam connection (2) between the lid (6) and the jacket (4) of the barrel is located in the beam path (S) between the X-ray source (10) and the X-ray detector (11).

The X-ray source (10), the X-ray detector (11) and the holding device (340) have adjusting elements, such as linear X-Y-Z adjusting elements, so the X-ray source (10) and the X-ray detector (11) and the folded-seam connection (2) to be tested can be precisely adjusted relative to one another so that the optical axis (12) between the X-ray source (10) and the X-ray detector (11) extends through the folded-seam connection (2). Furthermore, the optical axis (12) is intended to extend perpendicular to a tangent extending along the fold segment (3) to be tested, and exactly horizontal relative to the ground.

The holding device (30) has a holding frame (36), on which the barrel (1) is seated to rotate about its axis of symmetry (22), and can be fixed in an arbitrary orientation. The seating is effected by way of two rollers (34, 35) that are disposed at the ends of the barrel (1) and under the barrel (1), and extend parallel to one another and to the axis of symmetry (22). The barrel (1) is seated with its jacket (4) on these rollers (34, 35). One or both of the rollers (34, 35) can be driven for rotating the barrel (1). of course, wheels or the like that serve the same purpose can also be used in place of the rollers (34, 35).

The seating of the barrel (1) on the rollers (34, 35) simultaneously ensures that a barrel (1) located on the rollers (34, 35) is always in the correct position in the connecting direction between two adjacent rollers (34, 35), i.e., transversely to the longitudinal direction of the barrel (1), because the barrel (1) automatically assumes this position due to gravity. The seating by way of the rollers (34, 35) thus also serves in adjusting the barrel (1) in the holding device (30).

To adjust the barrel (1) in the longitudinal direction and fix the barrel (1) in the holding device (30), the rollers (34, 35) have a stopping flange (32, 33) at each end. Corresponding adjusting devices (31), such as compression-tension cylinders or spindles, bring the rollers (34, 35) with the end-side stopping flanges (32) into a precisely-defined position relative to the holding frame (36). When a barrel (1) is clamped in, the stopping flanges (32) on the side to be tested are brought into a stopped position, so the barrel (1) is located with the folded-seam connection (2) at the desired point on the optical axis (12) when the barrel impacts the stopping edges (32). The actuation of the corresponding adjusting devices (31) on the opposite end side of the barrel (1) then draws in the opposite stopping flanges (33), thereby clamping the barrel (1) fixedly in the defined position. This procedure efficiently compensates differences in length in the barrels to be tested.

The holding frame (36) is secured to a carrier (39) by way of a rotating pivot (37) to permit rotation about the axis (21) of the pivot (31) which extends perpendicular through the center point of the barrel (1). This rotating pivot is driven by a motor (38). The barrel (1) can therefore be rotated automatically by 180°, so the respective other fold (2) is located in the beam path (S), between the oppositely-located lid wall (5) and the jacket (4). To make an adjustment, the stopping flanges (32, 33) are them moved slightly apart again. The stopping flanges (33) that are now adjacent to the beam path (S) are moved into the adjustment position (zero position) and, subsequently, the oppositely-located stopping flanges (32) are drawn toward the barrel (1) for re-clamping the barrel (1).

A barrel (1) fixed in the holding device (30) in this manner can then be rotated about the vertical axis of rotation (20) extending perpendicular through the optical axis (12) and through the fold (2), with radiograms being generated continuously along predetermined angular increments; these radiograms are used to reconstruct the X-ray computer-tomographic image in the corresponding fold segment (3). For this purpose, the carrier (39), which holds the holding frame (36) in a pivotable connection, is rotatable in the axis of rotation (20) on a base (40), such as a pedestal part or the like, that is securely anchored to the floor. The barrel (1) rotates in an angular range of at least 180° while the sectional image is being generated. This angular range is limited by, among other things, the spatial measurements of the barrel (1) and the detector (11). As of certain barrel dimensions, rotating a barrel (1) by 360° and transilluminating it as a whole would require excessively-large X-ray detectors or X-ray sources; in other words, such systems would be very costly.

The quality of the generated image depends on the number if different radiograms, that is, the number of the angular increments, on the one hand. High-quality images are attained with 800 or more different individual increments or individual recordings. Images can also be generated with only 400 or even 200 angular increments, however. This is a function of the required image quality, and the respective type of fold seal. The image quality is further dependent on the resolution of the detector and the size of the focal point of the source. The pixel width in the reconstructed cross section is also significant for the resolution, which is in turn a function of the respective geometrical arrangement, such as the distance of the detector from the source and the reconstructed region.

For optimization, all of these parameters must be respectively adapted to the fold to be tested. In an embodiment for barrels having a height of 650 mm and a diameter of 280 mm, the distance between the X-ray tube (10) and the detector (11) is about 80 cm. It must be ensured that the position of the fold to be tested remains constant at about 10 $\mu$m relative to the axis of rotation (20). Suitable devices, such as an angle encoder, are used to determine the respective rotational angle of the barrel (1) with respect to the detector (11) with a higher resolution than ½°.

In this embodiment, the detector (11) possesses the following properties:

pixel width: 50 $\mu$m to 100 $\mu$m;
pixel height: 1 mm to 2 mm;
number of detector elements: 256 or 512;
detector length: about 20 mm;
energy range: about 200 kV;
dynamic range: >100:1; and
integration time: 0.02 sec. to 0.4 sec.

To attain a precise resolution between the different sheets of a folded-seam connection, the pixel width must be reduced to about 20 μm. This can be effected, for example, through an increase in the number of detector elements.

The X-ray tube (10) is operated up to 200 kV. With a one-meter distance between the tube (10) and the detector (11) and an approximate pixel width of 50 μm, the focal-point diameter should be about 1 mm. The power of the X-ray tube (10) is a function of the sensitivity of the detector (11) and the distance between the source (10) and the detector (11) and the desired measuring time, and can be selected accordingly. In a prototype of a line detector approximately possessing the properties listed above, a power of about 1 kW was determined with a 100-msec. integration time, that is, 20 to 40 sec. total measuring time.

The collection of measurement data and the reconstruction can be performed with a commercially-available PC, such as a 200-MHz Pentium.

Only specific angular regions ($\alpha_1, \alpha_2, \alpha_3, \alpha_4$) can be used to reconstruct the sectional image along the entire angular region ($\gamma$) that is traversed. In particular, the regions $\beta_1, \beta_2, \beta_3$, in which only one further fold is located at a different corner of the barrel (1) within the beam path (S), are kept in reserve. This second fold would lead to skewing. If a further wall of the barrel (1), for example the lid wall (5, 6) or a side wall (4), is located in the beam path (S) in specific angular regions, this wall can easily be taken into consideration in the reconstruction and possibly removed later. The only potential problem is further thickening along the jacket (4), which must likewise be removed later, or the corresponding radiograms cannot be used in the reconstruction.

It has been found that the radiograms in the remaining angular regions ($\alpha_1, \alpha_2, \alpha_3, \alpha_4$) suffice to generate satisfactory images.

The entire testing device is located in an X-ray shielding space (50), which only permits the maximum allowable X-ray dosage to exit. This space (50) has an opening (51) that can be tightly sealed, and through which the barrels (1) may be placed onto the holding frame (36) of the holding device (30), or removed from the frame, with a transfer device (not shown).

To test a complete barrel (1), the barrel is placed onto the holding frame (36) of the holding device (30), and a partial segment (3) of the fold is then brought into the beam path (S) between the lid (6) resting against the detector (11) with the jacket (4), and adjusted and fixed, as described above. The barrel (1) and the holding device (36) are then rotated about the axis of rotation (20) extending through the fold (2) and through the optical axis (12), and a sectional image recording is made. The clamping mechanism is then loosened, and the barrel (1) is rotated about its longitudinal axis (22) through the rotation of the rollers (35, 35), so a further partial segment of the fold (2) is located in the beam path (S). A new radiogram is then generated.

As soon as the fold (2) between the lid (6) and the wall (4) has been tested in this manner, the barrel (1) is rotated about the shaft (21) extending perpendicular through its center point, and the folded-seam connection (2) between the oppositely-located lid (5) and the wall (4) is tested in the same manner.

Of course, with an appropriate design of the holding frame and additional rotating and clamping means that may be disposed on the frame, it is also possible to retrofit the entire device such that it can also be used to test, for example, the folded-seam connection between a lid and the wall of a polygonal receptacle.

Figure 4:
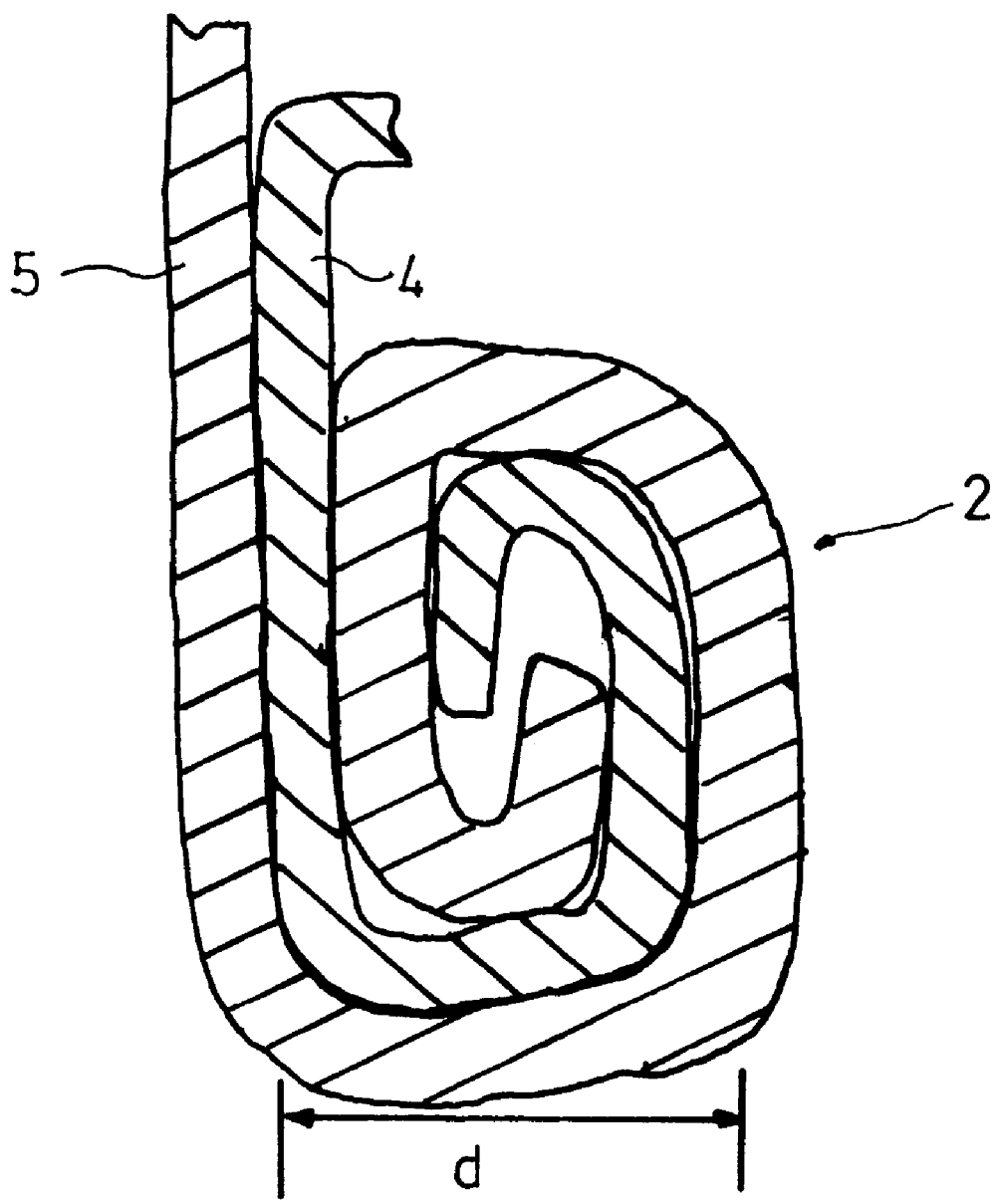
FIG. 4 a section through a folded-seam connection between a lid and the wall of a barrel.

FIG. 4 shows, by way of example, a section through a folded-seam connection (2) between a lid (5) and a wall (4), as can be generated as a computer-tomographic sectional image. The path (D) represented in this image is 5 mm. The image was generated with a pixel size of 20 μm, and the power of the X-ray tube (10) was 190 kV. It can be seen clearly that a very good resolution is attained, and that this method is especially well-suited for non-destructive testing of such folded-seam connections (2).

What is claimed is:

1. A method for testing an object (1), wherein a sectional image of the object is generated in at least a partial segment (3) of the object by means of an X-ray computer tomographer, the object (1) being clamped in a holding device within which at least a partial segment (3) is brought in a direction extending transversely to the segment into a beam path (S) between an X-ray source (10) and an X-ray detector (11) of the computer tomographer, the object (1) and the holding device (30) then being rotated in at least one angular region ($\gamma$), relative to the X-ray source (10) with the X-ray detector (11) about a first axis (20) that extends through the partial segment (3) and the beam path (S), the partial segment (3) remaining in the beam path (S), the X-ray detector (11) recording a radiogram in specific angular increments, and a cross-sectional image through the partial segment (3) being reconstructed from these radiograms, wherein the object (1) is a receptacle (1) having a folded-seam connection (2) between a lid (5) or bottom (6) and a jacket (4), and, to generate a sectional image through this folded-seam connection (2) in the radial direction, the holding device (30) is rotated about the first axis (20); then generate at least one further sectional image through at least one further partial segment of the folded-seam connection (2), the receptacle (1) being rotated along a circumference thereof in the holding device (30) until the further partial segment of the folded-seam connection (2) is located in the beam path (S), and the holding device (30) and the receptacle (1) are then rotated about the first axis (20) again to generate an image.

2. The method according to claim 1, wherein to generate sectional images through one or more partial segments of the folded-seam connection (2) between the lid (5) and the jacket (4), or the bottom (6) and the jacket (4), the holding device (30) and the receptacle (1) are preferably rotated by 180° about a second axis (21) that extends through the central point of the receptacle (1) and perpendicular to its axis of symmetry (22).

3. A device for executing the method according to claim 1, having at least one computer-tomography device that includes at least one X-ray source (10) and one X-ray detector (11), and having at least one holding device (30) that has clamping elements (31–33) for clamping a receptacle (1) provided with a folded-seam connection (2), the holding device (30) holding the receptacle (1) such that at least a partial segment (3) of the folded-seam connection (2) is located in the beam path (S) between the X-ray source (10) and the X-ray detector (11), and the holding device (30) being seated to rotate about a first axis (20) that extends perpendicular through an optical axis (12) between the X-ray detector (10) and the X-ray source (11) and through the partial segment (3), and the holding device (30) and/or the X-ray source (10) and/or the X-ray detector (11) having adjusting elements (32, 33) for orienting the receptacle (1) relative to the beam path (S) and a first axis (20), about which the holding device (30) can be rotated relative to the X-ray source (10) with the X-ray detector (11) such that, when the partial segment (3) is rotated about the first axis (20) extending through the beam path (S) in at least one angular region ($\delta$), the partial segment (3) of the folded-seam connection (2) remains in the beam path (S), wherein the receptacle (1) is a rotationally-symmetrical receptacle (1) having a jacket (4) and one or two end walls (5, 6) that are folded onto the jacket and the holding device (30) has elements (34, 35) for rotating the receptacle (1) about its axis of symmetry (22).

4. The device according to claim 3, wherein the holding device (30) includes elements for rotating the receptacle (1) about a second axis of rotation (21) extending through the center point of the receptacle (1).

5. The device according to claim 4, wherein the first axis of rotation (20) and the second axis of rotation (21) extend parallel to one another, and the receptacle (1) is held in the holding device (30) such that the axis of symmetry (22) of the receptacle (1) extends perpendicular to the first and second axes of rotation (20, 21).

6. The device according to claim 4, wherein the elements (34, 35) for rotating the receptacle (1) about its axis of symmetry (22) include at least two rollers (34, 35) that are disposed parallel to one another and to the axis of symmetry (22), and on which the receptacle (1) is seated with its jacket (4).

7. The device according to claim 4, wherein the holding device (30) has a holding frame (36) on which the receptacle (1) is seated to rotate about an axis of symmetry (22) and can be fixed in an arbitrary orientation, said holding frame (36) being rotatable connected to a carrier (39) in a second axis of rotation (21), said carrier (39) being rotatable connected to a base (40) in the first axis of rotation (20).

8. The device according to claim 4, wherein the holding device (30) is disposed, with the X-ray source (10) and the X-ray detector (11), in a shielding space (50), which has an opening (51) that can be closed and is provided for transferring a receptacle (1) into or from the holding device (30).

* * * * *